United States Patent [19]
Zhang

[11] Patent Number: 5,948,896
[45] Date of Patent: Sep. 7, 1999

[54] PROCESSES FOR PREPARING 13-DEOXY ANTHRACYCLINE DERIVATIVES

[75] Inventor: Xini Zhang, Hoover, Ala.

[73] Assignee: GEM Pharmaceuticals, Pelham, Ala.

[21] Appl. No.: 08/910,218

[22] Filed: Aug. 13, 1997

[51] Int. Cl.$^6$ .................................................. C07H 15/24
[52] U.S. Cl. ............................................................ 536/6.4
[58] Field of Search ............................................... 536/6.4

[56] References Cited

U.S. PATENT DOCUMENTS

| | | | |
|---|---|---|---|
| 3,590,028 | 6/1971 | Arcamone et al. | 260/210 |
| 3,616,242 | 10/1971 | Belloc et al. | 195/80 |
| 4,067,969 | 1/1978 | Penco et al. | 424/180 |
| 4,088,569 | 5/1978 | Douglas | 208/206 |
| 4,134,903 | 1/1979 | Masi et al. | 260/365 |
| 4,247,545 | 1/1981 | Cassinelli et al. | 424/181 |
| 4,309,503 | 1/1982 | Cassinelli et al. | 435/78 |
| 4,345,070 | 8/1982 | Suarato et al. | 536/17 A |
| 4,353,894 | 10/1982 | Acton et al. | 424/180 |
| 4,411,834 | 10/1983 | Cassinelli et al. | 260/365 |
| 4,465,671 | 8/1984 | Angelucci et al. | 536/6.4 |
| 4,515,720 | 5/1985 | Hauser et al. | 260/351.1 |
| 4,839,346 | 6/1989 | Bargiotti et al. | 514/34 |
| 4,891,360 | 1/1990 | Angelucci et al. | 514/34 |
| 4,939,282 | 7/1990 | Angelucci et al. | 536/6.4 |
| 4,985,548 | 1/1991 | Caruso et al. | 536/6.4 |
| 4,987,126 | 1/1991 | Bargiotti et al. | 536/6.4 |
| 5,037,970 | 8/1991 | Angelucci et al. | 536/6.4 |
| 5,138,042 | 8/1992 | Angelucci et al. | 536/6.4 |
| 5,412,081 | 5/1995 | Angelucci et al. | 536/6.4 |
| 5,532,218 | 7/1996 | Bargiotti et al. | 514/34 |

OTHER PUBLICATIONS

Aston, E.M., "Unresolved Structure–Activity Relationships in Anthracycline Analogue Development.", *Anthracycline Antibiotics: New Analogues, Methods of Delivery, and Mechanisms of Action*, Waldemar Priebe, Ed., ACS Symposium Series 574, American Chemical Society, (1995) pp. 1–13.

Cassinelli, G. et al., "13–Deoxycarminomycin, A new Biosynthetic Anthracycline.", *J. Natural Products*, (1985) 48 (3) 435–439.

Smith, T.H., et al., "Adriamycin Analogues. 2. Synthesis of 13–Deoxyanthracyclines," *Journal of Medicinal Chemistry*, vol. 21, No. 3, 1978, pp. 280–283.

*Primary Examiner*—Amelia Owens
*Attorney, Agent, or Firm*—Pollock, Vande Sande & Amernick

[57] ABSTRACT

A process for the preparation of 13-deoxy deoxyanthracycline derivatives.

12 Claims, No Drawings

PROCESSES FOR PREPARING 13-DEOXY ANTHRACYCLINE DERIVATIVES

FIELD OF THE INVENTION

The invention relates to 13-deoxy anthracycline derivatives and improved methods for preparing these 13-deoxy anthracycline derivatives.

BACKGROUND OF THE INVENTION

The most well-known anthracycline anticancer drugs are doxorubicin and daunorubicin, which contain a 13-keto group. Doxorubicin, disclosed in U.S. Pat. No. 3,590,028, has a wide spectrum of anticancer utility and is used in the treatment of leukemias, lymphomas, and solid tumors. Daunorubicin, disclosed in U.S. Pat. No. 3,616,242, is useful in the treatment of acute leukemias. However, the utility of these drugs is limited by a serious side effect of cardiotoxicity so that the total amount of drug that can be given to a patient cannot exceed 550 mg/M$^2$ (E. A. Lefrak et al., Cancer, 32:302, 1973). Even at or near the recommended maximum total cumulative dosage (430–650 mg/M$^2$) significant and persistent heart dysfunction occurs in 60% of patients and 14% develop congestive heart failure (A. Dresdale et al., Cancer, 52:51, 1983). Thus, while these drugs are useful to inhibit the growth of cancerous tumors, the patient may die of congestive heart failure because of the severe cardiotoxic side effect of the drugs.

Some researchers believe that the cardiotoxicity is a result of free radical generation by the quinone moiety of the anthracycline molecule (J. Dorowshow et al., J. Clin. Invest., 68:1053, 1981; D. V. Unverferth et al., Cancer Treat. Rev., 9:149, 1982; J. Goodman et al., Biochem. Biophys. Res. Commun., 77:797, 1977; J. L. Zweier, J. Biol. Chem., 259:6056, 1984). On the other hand, there is good evidence that free radical generation may not be a major mechanism of cardiotoxicity because the drugs still produce cardiac damage in the presence of free radical scavengers (J. F. VanVleet et al., Am. J. Pathol., 99:13, 1980; D. V. Unverferth et al., Am. J. Cardiol., 56:157, 1985; C. Myers et al., Seminars in Oncology, 10:53, 1983; R. H. M. Julicher et al., J. Pharm. Pharmacol., 38:277, 1986; E. A. Porta et al., Res. Comm. Chem. Pathol Pharmacol., 41: 125, 1983).

It has also been found that inhibition of free radical generation does not eliminate the cardiotoxicity of these anthracyclines (P. S. Mushlin et al., Fed. Proc., 45:809, 1986). This research shows, instead, that the cardiotoxicity of doxorubicin and daunorubicin, as manifested by a reduction in myocardial contractility, is dependent upon the metabolic reduction of the 13-keto moiety to a 13-dihydro metabolite. In test systems where doxorubicin is not metabolized appreciably to the 13-dihydro compound cardiotoxic effects are observed only at very high concentrations (200–400 micrograms/ml) (P. S. Mushlin et al., Fed. Proc., 44:1274, 1985; R. D. Olson et al., Fed. Proc., 45:809, 1986). In contrast, the 13-dihydro metabolites, doxorubicinol and daunorubicinol, produce cardiotoxicity in these same test systems at relatively low concentrations (1–2 micrograms/ml, R. D. Olson et al., Proceed. Am. Assoc. Cancer Res., 26:227, 1985; R. D. Olson et al., Proceed. Am. Assoc. Cancer Res., 28:441, 1987).

If doxorubicin is allowed to remain in the test systems even for short periods of time some metabolic conversion occurs and the 13-dihydro metabolite is formed in sufficient quantity so that cardiotoxicity begins to develop (L. Rossini et al., Arch. Toxicol. suppl., 9:474, 1986; M. Del Tocca et al., Pharmacol. Res. Commun., 17:1073, 1985). Substantial evidence has, thus, accumulated that the cardiotoxicity of drugs such as doxorubicin and daunorubicin results from the potent cardiotoxic effects produced by their 13-dihydro metabolites (P. Mushlin et al., Rational Drug Therapy, 22:1, 1988; S. Kuyper et al., FASEP Journal, 2:A1133, 1988; R. Boucek et al., J. Biol. Chem., 262:15851, 1987; and R. Olson et al., Proc. Natl. Acad. Sci., 85:3585, 1988).

The present invention makes use of the fact that the 13-deoxy forms of doxorubicin, daunorubicin, or other similar anthracyclines will not be metabolically converted to cardiotoxic 13-dihydro forms, thus providing a means for administering compounds of the present invention in non-cardiotoxic amounts without limitation of total cumulative dosage.

Known processes for preparing these compounds have relatively low yields, on the order of about 30% (see Smith, et al., J. Med. Chem. 1978 21, 280–283).

SUMMARY OF THE INVENTION

The present invention aims to solve the above-described deficiencies of known processes for preparing 13-deoxy anthracycline derivatives.

Accordingly, an object of the present invention is to provide improved processes for preparing 13-deoxy anthracycline derivatives that provides an improved yield as compared to known processes.

In accordance with these and other objects and advantages, the preferred aspects of the present invention provide a process for the preparation of 13-deoxy anthracycline derivatives.

Generally, anthracyclines of the formula I

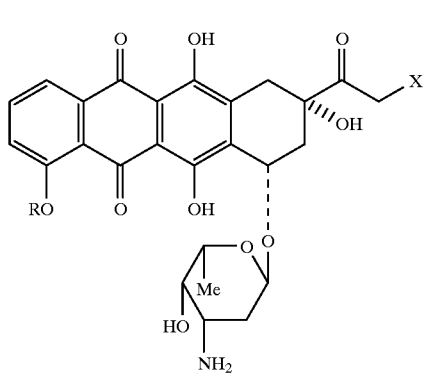

are readily converted to 13-tosylhydrazones according to known methods. Anthracycline 13-tosylhydrazones are reduced to 13-deoxy anthracycline derivatives with sodium cyanoborohydride under acidic conditions. The products are purified by preparative chromatography without extraction steps. The processes have been found to have a yield of from about 70% to about 80%.

Additional preferred aspects of the present invention provide a process for the preparation of 13-deoxy deoxyanthracycline derivatives. The process includes forming an acidic solution of anthracycline 13-tosylhydrazone with cyanoborohydride. The solution is gently refluxed. The reaction mixture is cooled. Saturated aqueous NaHCO$_3$ is added to the solution, followed by a halocarbon solvent. The mixture is filtered. The filtrate is acidified. The filtrate is subjected to preparative chromatography to isolate the 13-deoxy deoxyanthracycline derivatives.

Further preferred aspect of the present invention provide a process for the preparation of 13-deoxy deoxyanthracycline derivatives. The process includes forming a solution by dissolving about 1 g of doxorubicin 13-tosylhydrazone hydrochloride and about 2.4 g of p-toluene sulfonic acid in about 50 mL of anhydrous methanol. About 0.8 g of sodium cyanoborohydride is added to the solution. The solution is heated to a temperature of from about 68° C. to about 72° C. The solution is gently refluxed for about one hour under a nitrogen atmosphere. The reaction mixture is concentrated to about 20 ml. The reaction mixture is cooled in a freezer to a temperature of from about 0° C. to about 4° C. About 2 ml of saturated aqueous sodium bicarbonate is added to the reaction mixture. About 200 ml of chloroform is added to the reaction mixture. Anhydrous sodium sulfate is added to the reaction mixture. Salts are filtered out. The filtrate is acidified with hydrogen chloride in diethyl ether. The solution is run through a silica gel column. The column is further washed with chloroform/methanol until the eluate is colorless. A fraction containing the product is eluted with methanol. The methanol eluate is evaporated. Residue resulting from the evaporation is dissolved in 30% acetonitrile in ammonium formate buffer. The product is isolated by preparative HPLC using a phenyl column. The product is separated from other impurities using an acetonitrile/ammonium formate gradient. The HPLC purified fraction is then lyophilized to produce about 600 mg of 13-deoxy doxorubicin hydrochloride.

Still other objects and advantages of the present invention will become readily apparent to those skilled in the art from the following description. The detailed description shows and describes only preferred embodiments of the invention so as to illustrate the best mode contemplated for carrying out the invention. As those skilled in the art will realize, the invention includes other and different embodiments. Details of the invention may be modified in various respects, without departing from the invention. Accordingly, the drawings and description should be regarded as illustrative in nature and not as restrictive.

DETAILED DESCRIPTION OF THE INVENTION

The present invention provides improved methods for forming 13-deoxy anthracycline derivatives. The table below provides examples of 13-deoxy anthracycline derivatives that may be synthesized according to the present invention. As discussed above, compounds such as those shown in the table below are known to have anti-tumor properties.

Unlike known processes, the processes of the present invention are less temperature sensitive. For example, the processes may be carried out at a temperature of from about 0° C. to about 75° C. Preferably, the processes are carried out at a temperature of from about 65° C. to about 75° C. More preferably, the process are carried out at a temperature of from about 68° C. to about 72° C. Temperatures over about 72° C. typically result in decomposition of the reactants and products.

The process of the present invention includes a number of general conditions. For example, the processes preferably are carried out in acidic conditions. In other words, the pH should be about 6.5 or less. Known processes for preparing the above compounds, which employ basic conditions within the reaction mixture, have been found to cause decomposition of the reactants and products.

Additionally, both oxygen and water should be excluded from the reactions. Preferably, the reaction is conducted in a nitrogen or inert gas atmosphere, using anhydrous solvents.

The processes of the present invention result in a much higher yield than known processes for preparing the compounds. For example, known processes have been found to have a yield of about 30%. On the other hand, processes of the present invention have been found to have a yield of from about 70% to about 80%.

In accordance with the above, the present invention provides processes for preparing compounds of the general formula I above.

The following provides an example of the transformation of the molecule as it progresses through the process.

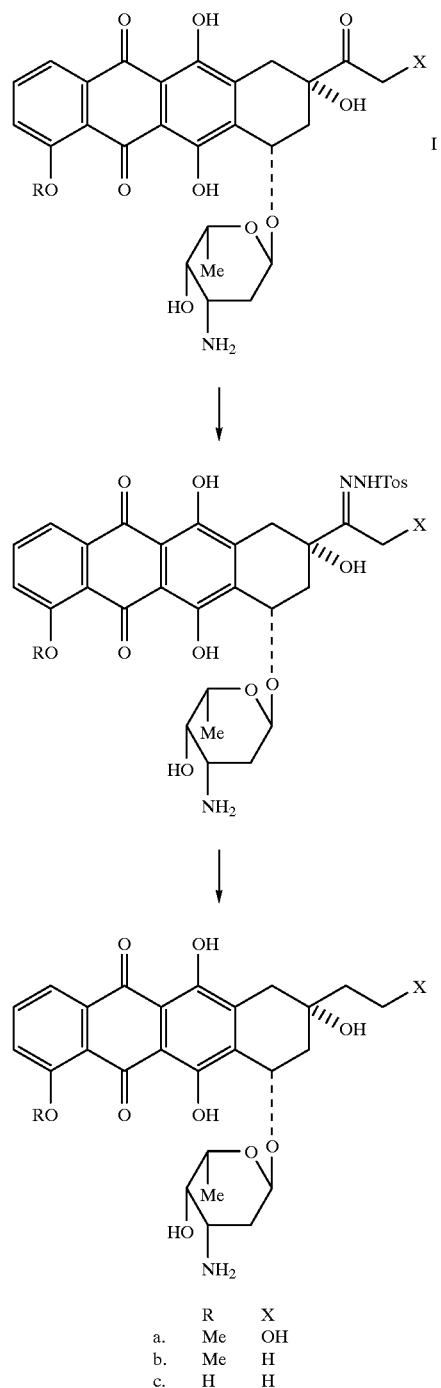

| | R | X |
|---|---|---|
| a. | Me | OH |
| b. | Me | H |
| c. | H | H |

The following flowchart illustrates an example of an embodiment of a method according to the present invention for producing 13-deoxydoxorubicin, which is a 13-deoxy anthracycline derivative.
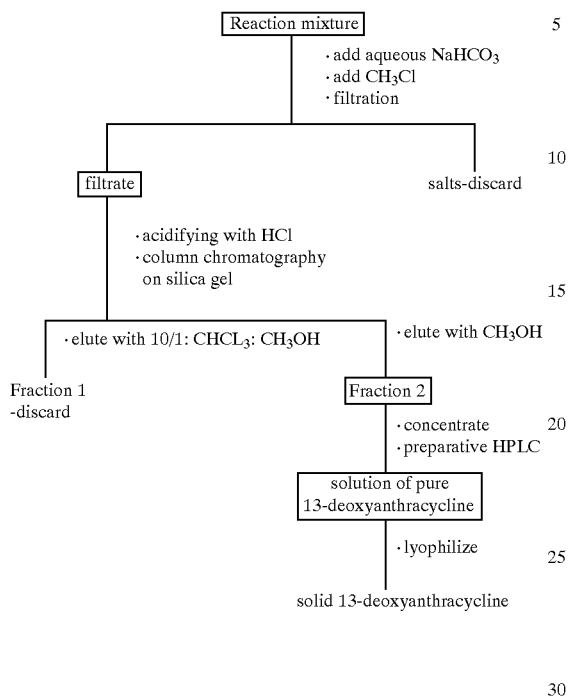
The following represents examples of anthracycline derivatives, the synthesis of which is disclosed herein.
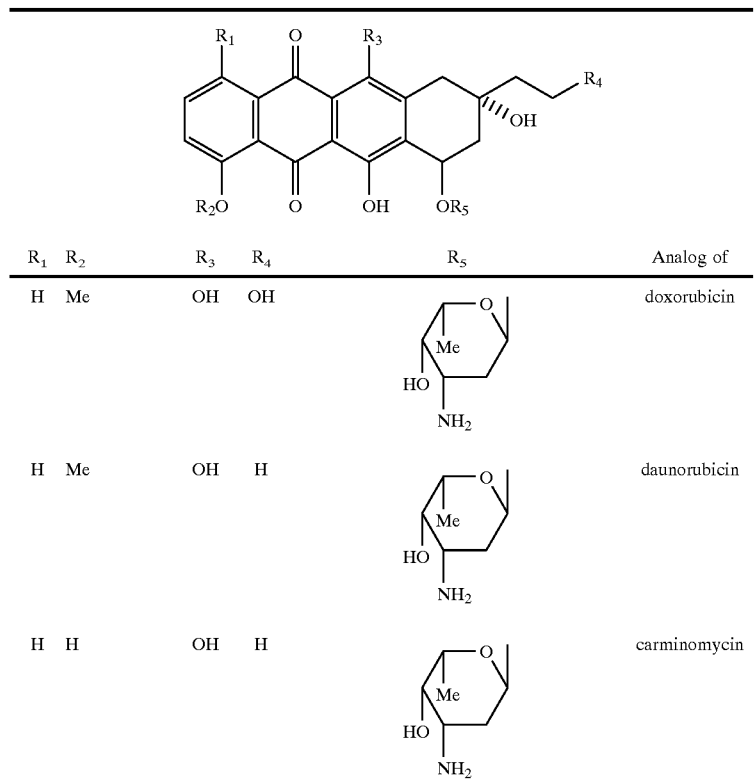
| $R_1$ | $R_2$ | $R_3$ | $R_4$ | $R_5$ | Analog of |
|---|---|---|---|---|---|
| H | Me | OH | OH | (sugar with Me, HO, $NH_2$) | doxorubicin |
| H | Me | OH | H | (sugar with Me, HO, $NH_2$) | daunorubicin |
| H | H | OH | H | (sugar with Me, HO, $NH_2$) | carminomycin |

-continued

| $R_1$ | $R_2$ | $R_3$ | $R_4$ | $R_5$ | Analog of |
|---|---|---|---|---|---|
| OH | H | H | H | [sugar trisaccharide with Me, NH$_2$, OH groups] | |
| H | Me | OH | OH | [sugar: HO, O, Me, NH$_2$] | epirubicin |
| H | H, no O between $R_2$ and molecule | OH | H | [sugar: O, Me, HO, NH$_2$] | idarubicin |
| H | H, no O between $R_2$ and molecule | OH | OH | [sugar: HO, O, CH$_3$, HO, I] | annamycin |

In the compounds, $R_5$ may be a modified version of different anthrcycline analogs. Also, The D ring may be fluorinated.

Generally, processes according to the present invention include forming a solution of a 13-deoxy anthracycline. The solution is gently refluxed. Then, the reaction mixture may be cooled. According to one example, the reaction mixture is cooled to a temperature of from about 0° C. to about 4° C. A base is then added to the reaction mixture. The base may be cold. For example, the base be at a temperature of from about 0° C. to about 4° C. One example of a base is saturated aqueous NaHCO$_3$. A halocarbon solvent may be added to the reaction mixture. The halocarbon solvent may be added to the reaction mixture simultaneously with the base. The halocarbon solvent may be cold. For example, the halocarbon solvent may be at a temperature of from about 0° C. to about 4° C. An example of a halocarbon solvent that may be utilized is CHCl$_3$. The reaction mixture may then be filtered. The filtration may also take place at a reduced temperature. For example, the filtration may take place at a temperature of from about 4° C. to about 15° C.

Addition of the base and the halocarbon solvent described above preferably initiates a hydrolysis precipitation. It is the precipitate of inorganic salts that may be filtered out of the reaction mixture. After filtration, the filtrate may be acidified. The filtrate may be subjected to column chromatography on silica gel. Hydrophobic impurities may be isolated by eluting with less polar solvents. 13-deoxy anthracycline products may then be eluted and the elute further purified.

Preferably, the processes according to the present invention include forming a solution of anthracycline 13-tosylhydrazones in anhydrous methanol with p-toluenesulfonic acid and sodium cyanoborohydride. The solution is refluxed gently under nitrogen and then cooled. Saturated aqueous sodium bicarbonate and chloroform are added. Salts precipitated are filtered and the filtrate is acidified with hydrogen chloride in diethyl ether and then isolated on a silica gel column. The hydrophobic impurities resulted from decomposition are eluted with chloroform and methanol mixed solution. The products, 13-deoxy anthracyclines, are eluted with methanol. The methanol elute is further purified by preparative HPLC.

The following provides an example of a process according to the present invention.

EXAMPLE

Preparation of 13-Deoxy doxorubicin hydrochloride 1 g of doxorubicin 13-tosylhydrazone hydrochloride and 2.4 g of p-toluene sulfonic acid are dissolved in 50 mL of anhydrous methanol. To this solution 0.8 g of sodium cyanoborohydride is added. The resulting solution is heated to 68–72° C. and kept at gentle reflux for one hour under nitrogen atmosphere.

Then, the reaction mixture is concentrated to about 20 ml and cooled in a freezer to 0–4° C. 2 ml of saturated aqueous sodium bicarbonate is added followed by 200 ml of chloroform. Anhydrous sodium sulfate is added and the salts are filtered after shaking. The filtrate is acidified with hydrogen chloride in diethyl ether.

The solution is then run through a silica gel column (2.5×5 cm). The column is further washed with chloroform/methanol (10/1) until the eluate is colorless. The bound fraction containing the product is eluted with methanol. The methanol elute is evaporated and residue is dissolved in 30% acetonitrile in ammonium formate buffer (pH=4.0, 0.5%) and isolated by preparative HPLC. A phenyl column is used and separation of the product from the other impurities is achieved by using an acetonitrile/ammonium formate gradient (from 27% to 30% acetonitrile for 30 min). The HPLC purified fraction is lyophilized to give solid 13-deoxy doxorubicin hydroformate, which is then dissolved in methanal containing hydrogen chloride. The solvent is evaporated and the produce is precipitated in methanol/ethyl ether to give 600 mg 13-deoxy doxorubicin hydrochloride. The yield is 80%.

TLC: $R_f = 0.38$  $CH_3Cl : MeOH : H_2O$
$\phantom{TLC: R_f = 0.38\ \ }30\phantom{xxx}10\phantom{xxx}1$ U.V.: $\lambda_{max}$=233, 252, 293, 485 nm
MS: 530 (M+H),

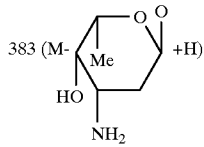

383 (M-  ... +H)

$^1$HNMR (methanol $d_4$): (see below)
δ 1.30 (d, 3H, 6'-H$_3$),
1.85 (m, 2H, 13-H$_2$),
2.05 (m, 2H, 10-H$_2$),
2.60 (d, 1H, 12-H),
3.05 (d, 1H, 12-H),
3.55 (m, 1H, 5'-H),
3.90 (m, 2H, 14-H$_2$),
4.05 (m, 3H, O-CH$_3$),
4.25 (m, 1H, 4'-H),
4.95 (m, 1H, 3'-H),
5.40 (m, 1H, 1'-H),
7.50 (dd, 1H, 3-H), and
7.80 (m, 2H, 1-and 2-H)

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A process for the preparation of 13-deoxy anthracycline derivatives, said process comprising the steps of:
   forming a solution of anthracycline 13-tosylhydrazone in anhydrous methanol with p-toluenesulfonic acid and sodium cyanoborohydride;
   gently refluxing the solution at a temperature of up to about 75° C.; in an absence of oxygen, in an absence of water, and under nitrogen;
   cooling the solution;
   adding saturated aqueous sodium bicarbonate and chloroform to the solution to form a precipitate;
   filtering the precipitate;
   acidifying the filtrate with hydrogen chloride in diethyl ether;
   isolating salt contained in the filtrate on a silica gel column;
   eluting the hydrophobic impurities resulting from decomposition of the salts with a mixed solution of chloroform and methanol;
   eluting the 13-deoxy anthracycline products with methanol; and
   further purifying the methanol elute by preparative HPLC.

2. The process according to claim 1, wherein said solution has a pH of 6.5 or less.

3. The process according to claim 2, wherein said refluxing is carried out at a temperature of from about 68° C. to about 72° C.

4. The process according to claim 2, wherein said refluxing is carried out at a temperature of from about 65° C. to about 75° C.

5. The process according to claim 1, wherein said refluxing is carried out in an atmosphere of nitrogen.

6. The process according to claim 1, wherein said refluxing is carried out in an atmosphere of an inert gas.

7. The process according to claim 1, wherein said process results in a yield of from about 70% to about 80%.

8. The process of claim 1 wherein said 13-deoxy anthracycline is 13-deoxy doxorubicin.

9. The process of claim 1 wherein said 13-deoxy anthracycline is selected from the group consisting of 13-deoxy doxorubicin, 13-deoxy daunorubicin, 13-deoxy corminomycin, 13-deoxy epirubicin, 13-deoxy idarubicin, and 13-deoxy annamycin.

10. A process according to claim 1 for preparing anthracycline derivatives, said process comprising the steps of:
    forming a solution by dissolving doxorubicin 13-tosylhydrazone hydrochloride and p-toluene sulfonic acid in anhydrous methanol;

adding sodium cyanoborohydride to the solution;

heating the solution to a temperature of from about 68° C. to about 72° C.;

gently refluxing the solution for about one hour under a nitrogen atmosphere;

concentrating the reaction mixture;

cooling the reaction mixture to a temperature of from about 0° C. to about 4° C.;

adding saturated aqueous sodium bicarbonate to the reaction mixture;

adding chloroform to the reaction mixture;

adding anhydrous sodium sulfate;

filtering salts resulting from the addition of the anhydrous sodium sulfate after shaking;

acidifying the filtrate with hydrogen chloride in diethyl ether;

running the solution through a silica gel column;

further washing the column with chloroform/methanol until the eluate is colorless;

eluting with methanol a fraction containing the product;

evaporating the methanol eluate;

dissolving residue resulting from the evaporation acetonitrile in ammonium formate buffer;

isolating the produce by preparative HPLC using a phenyl column;

separating the product from other impurities using an acetonitrile/ammonium formate gradient; and lyophilizing the HPLC purified fraction to produce 13-deoxy doxorubicin hydrochloride.

11. A process for the preparation of 13-deoxy anthracycline derivatives, said process comprising the steps of:

forming a solution of anthracycline 13-tosylhydrazone;

refluxing the solution at a temperature of up to about 75° C., in an absence of oxygen, and in an absence of water;

cooling the reaction mixture;

adding saturated aqueous $NaHCO_3$, adding a halocarbon solvent to the reaction mixture;

filtering the reaction mixture;

acidifying the filtrate; and subjecting the filtrate to chromatography to isolate the 13-deoxy anthracycline derivatives.

12. A process for the preparation of 13-deoxy anthracycline derivatives, said process comprising the steps of:

forming a solution by dissolving about 1 g of doxorubicin 13-tosylhydrazone hydrochloride and about 2.4 g of p-toluene sulfonic acid in about 50 mL of anhydrous methanol;

adding about 0.8 g of sodium cyanoborohydride to the solution;

heating the solution to a temperature of from about 68° C. to about 72° C.;

gently refluxing the solution for about one hour under a nitrogen atmosphere;

concentrating the reaction mixture to about 20 ml;

cooling the reaction mixture in a freezer to a temperature of from about 0° C. to about 4° C.;

adding about 2 ml of saturated aqueous sodium bicarbonate to the reaction mixture;

adding about 200 ml of chloroform to the reaction mixture;

adding anhydrous sodium sulfate;

filtering salts resulting from the addition of the anhydrous sodium sulfate after shaking;

acidifying the filtrate with hydrogen chloride in diethyl ether;

running the solution through a silica gel column;

further washing the column with chloroform/methanol until the eluate is colorless;

eluting with methanol a fraction containing the product;

evaporating the methanol eluate;

dissolving residue resulting from the evaporation in 30% acetonitrile in ammonium formate buffer;

isolating the produce by preparative HPLC using a phenyl column;

separating the product from other impurities using an acetonitrile/ammonium formate gradient; and lyophilizing the HPLC purified fraction to produce about 600 mg of 13-deoxy doxorubicin hydrochloride.

* * * * *